US00PP15417P2

(12) United States Plant Patent
Boeder

(10) Patent No.: US PP15,417 P2
(45) Date of Patent: Dec. 14, 2004

(54) ***CHRYSANTHEMUM* PLANT NAMED 'BABITA'**

(50) Latin Name: *Chrysanthemum morifolium*
Varietal Denomination: Babita

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 10/756,375

(22) Filed: Jan. 14, 2004

(51) Int. Cl.[7] ..... A01H 5/00
(52) U.S. Cl. ..... Plt./289
(58) Field of Search ..... Plt./289

*Primary Examiner*—Anne Marie Grunberg
*Assistant Examiner*—Annette H Para
(74) *Attorney, Agent, or Firm*—Parkhurst & Wendel, L.L.P.

(57) ABSTRACT

A *Chrysanthemum* plant named 'Babita' characterized by its small sized blooms with orange ray florets and prolific branching; natural season flower date September 8–13; blooming for a period of 5 weeks.

2 Drawing Sheets

BACKGROUND OF THE INVENTION

'Babita' is a product of a breeding and selection program for outdoor pot mums (garden mums) which had the objective of creating new *Chrysanthemum* cultivars with a decorative type flower, a natural season flower date around September 8–13; blooming for a period of 5 weeks. The new plant of the present invention comprises a new and distinct cultivar of *Chrysanthemum* plant 'Babita' is a seedling resulting from the crossing of the female parent '22.0724' with a mixed population of *Chrysanthemum* plants serving as male parents maintained under the control of the inventor for breeding purposes. The new and distinct cultivar was discovered and selected as one flowering plant by Mark Roland Boeder on a cultivated field in Rijsenhout Holland in September 2001. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
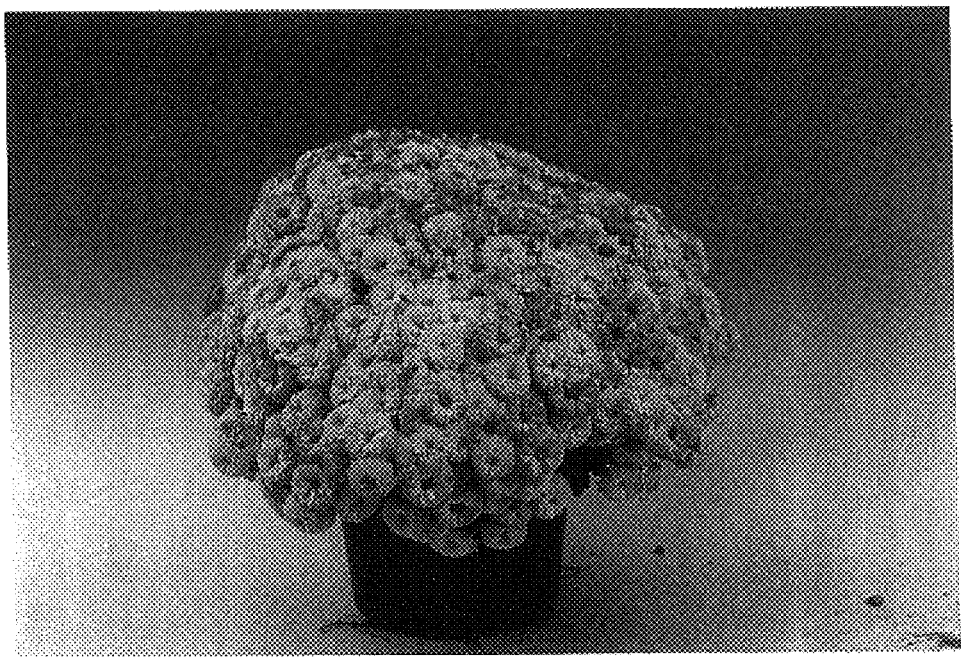
FIG. 1 shows a plant of the cultivar in full bloom.
Figure 2:
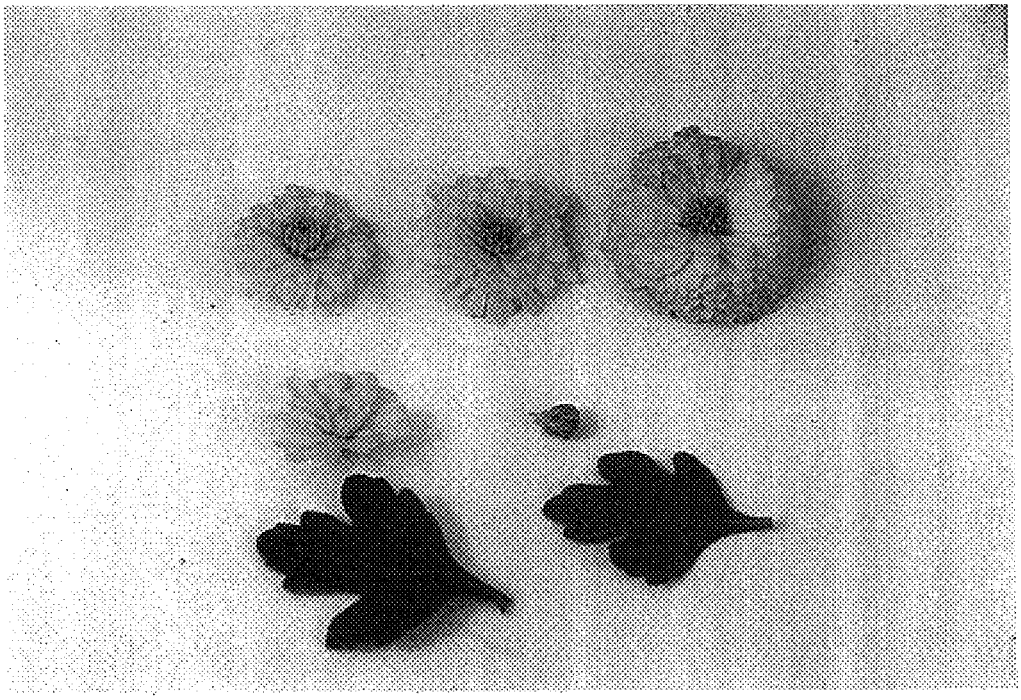
FIG. 2 shows the various stages of bloom and foliage of the new cultivar.

This new variety of *Chrysanthemum* is of the botanical classification *Chrysanthemum morifolium.* The observations and measurements were gathered from plants grown out door in Rijsenhout, Holland under natural day length and temperature and planted in week 23 in 2002. The natural blooming date of this crop was September 8–13 (week 37). The average height of the plants was 35 cm. No growth retardants were used. No tests were done on disease or insect resistance or susceptibility. No tests were done on cold or drought tolerance. This new variety produces small sized blooms with orange ray florets blooming for a period of 5 weeks.

From the cultivars known to inventor the most similar existing cultivar in comparison to 'Babita' is 'Zesty Barbara' (U.S. Plant Pat. No. 9,569). When 'Zesty Barbara' and 'Babita' are being compared the following differences are noticed. The differences of 'Zesty Barbara' and 'Babita' are (1) Ray-floret color. The ray-florets of 'Zesty Barbara' are purple colored, while those of 'Babita' are soft orange with purple edges. (2) Color of center of immature flowers. The center of 'Zesty Barbara' is soft green, while that of 'Babita' is orange.

The following is a description of the plant and characteristics that distinguish 'Babita' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1. Botanical Description of cultivar 'Babita'

Bud:
- *Size.*—Small; cross-section 0.8 cm, height 0.5 cm.
- *Outside color.*—Yellow-green 145C.
- *Involucral bracts.*—2 rows, length 7 mm, width 3 mm.
- *Involucral bracts among disc-florets.*—Not present.
- *Involucral bracts color.*—Yellow-green 148C.

Bloom:
- *Type.*—Decorative.
- *Size.*—Small.
- *Fully expanded.*—4 cm.
- *Peduncle length.*—7.5 cm.
- *Peduncle color.*—Yellow-green 148C.
- *Number of blooms per branch.*—Approx. 8 blooms per branch.
- *Performance on the plant.*—5 weeks.
- *Seeds.*—Produced in small quantities, ovate grey-brown 199A, 1½ mm in length.
- *Fragrance.*—Typical *Chrysanthemum*, slightly.

Color:
- *Center of the flower.*—Immature Greyed-orange 172C. Mature Yellow-orange 15B.
- *Color of upper surface of the ray-florets.*—Yellow-orange 23D with Greyed-purple 186C at edges.

*Color of the lower surface of the ray-florets.*—Orange 24D.
*Tonality from distance.*—A garden mum with orange flowers and a center of darker shade.
*Color of upper surface of ray-florets at aging of the plant.*—Yellow-orange 23D and Greyed-purple 186C.

Ray florets:
*Texture.*—Upper and under side smooth.
*Number.*—150.
*Cross-section.*—Flat.
*Longitudinal axis of majority.*—Straight.
*Length of corolla tube.*—Short, 0.3 cm.
*Ray-floret margin.*—Entire.
*Ray-floret length.*—1.5 cm.
*Ray-floret width.*—0.4 cm.
*Ratio length/width.*—Medium.
*Shape of tip.*—Rounded.

Disc florets:
*Disc diameter.*—0.3 cm.
*Distribution of disc florets.*—Few, visible only in mature stage.
*Shape.*—Tubular.
*Color.*—Yellow-green 145C.
*Receptacle shape.*—Conical raised.

Reproductive organs:
*Stamen.*—Present in disc florets only.
*Stamen color.*—Yellow-green 144A.
*Pollen.*—Produced in small amount.
*Pollen color.*—Yellow 7A.
*Styles.*—Thick.
*Style color.*—Yellow 13A.
*Style length.*—4 mm.
*Stigma color.*—Yellow-green 144A.
*Stigma width.*—1 mm.
*Ovaries.*—Enclosed in calyx.

Plant:
*Form.*—A garden mum outdoor mounded and round.
*Growth habit.*—Spreading.
*Growth rate.*—High.
*Height.*—35 cm.
*Width.*—45 cm.
*Stem color.*—Yellow-green 146C.
*Stem strength.*—Strong.
*Stem brittleness.*—Not brittle.
*Stem anthocyanin coloration.*—Absent.
*Internode length.*—2.5 cm.
*Length of lateral branch.*—From top to bottom 15 cm.
*Lateral branch color.*—Yellow-green 147C.
*Lateral branch, attachment.*—Medium strength.
*Branching* (*average number of lateral branches*).—Good with 7 breaks after pinching.
*Natural season blooming date.*—September 8–13.

Foliage:
*Leaf color.*—Upper side Yellow-green 147A. Under side Green 138B.
*Color midvein.*—Upper side Green 139D. Under side Green 138D.
*Size.*—Small; length 2.5 cm, width 2 cm.
*Quantity* (*number per lateral branch*).—25.
*Shape.*—Cordiform.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Rounded.
*Margin of sinus between lateral lobes.*—Diverging.
*Shape of base.*—Obtuse.
*Apex.*—Rounded.
*Petiole length.*—0.2 cm.
*Petiole color.*—Green 139D.

TABLE 2

| Differences with the comparison variety | | |
|---|---|---|
| | 'Babita' | 'Zesty Barbara' |
| Color of ray-florets | Yellow-orange 23D with Greyed purple 186C | Red-purple 58A |
| Color of disc in immature flowers | Greyed-orange 172C | Yellow-green 144C |

I claim:

1. A new and distinct variety of *Chrysanthemum* plant as described and illustrated.

* * * * *